United States Patent [19]
Tomcufcik et al.

[11] Patent Number: 4,486,430
[45] Date of Patent: Dec. 4, 1984

[54] METHOD OF TREATING ARTHRITIC DISEASE

[75] Inventors: Andrew S. Tomcufcik, Old Tappan, N.J.; Adolph E. Sloboda, New City, N.Y.

[73] Assignee: American Cyanamid Company, Stamford, Conn.

[21] Appl. No.: 134,593

[22] Filed: Mar. 27, 1980

Related U.S. Application Data

[63] Continuation-in-part of Ser. No. 17,796, Mar. 5, 1979, Pat. No. 4,261,892, which is a continuation-in-part of Ser. No. 895,572, Apr. 12, 1978, abandoned.

[51] Int. Cl.$^3$ ............................................. A61K 31/53
[52] U.S. Cl. .................................................... 424/249
[58] Field of Search ........................................ 424/249

[56] References Cited

U.S. PATENT DOCUMENTS 3,577,417  5/1971  Cantrall et al. ...................... 544/197
3,706,741 12/1972  Popaioannou ....................... 544/197

Primary Examiner—Stanley J. Friedman
Attorney, Agent, or Firm—Edward A. Conroy, Jr.

[57] ABSTRACT

This disclosure describes compositions of matter useful as anti-inflammatory agents and as inhibitors of the progressive joint deterioration characteristic of arthritic disease and the methods of meliorating inflammation and of inhibiting joint deterioration in mammals therewith, the active ingredients of said compositions of matter being certain 2,4,6-tris(substituted-amino)-s-triazines.

3 Claims, No Drawings

METHOD OF TREATING ARTHRITIC DISEASE

CROSS REFERENCE TO RELATED APPLICATION

This application is a continuation-in-part of our application Ser. No. 17,796, filed Mar. 5, 1979, now U.S. Pat. No. 4,261,892, which is a continuation-in-part of our abandoned application Ser. No. 895,572, filed Apr. 12, 1978.

BRIEF SUMMARY OF THE INVENTION

This invention relates to novel compositions of matter useful as anti-inflammatory agents and as inhibitors of the progressive joint deterioration characteristic of arthritic disease. More particularly, it relates to therapeutic compositions containing certain $N_2$, $N_4$, $N_6$-tris(substituted)melamines which meliorate inflammation and inhibit arthritic joint deterioration in mammals. The invention includes the new compositions of matter and the methods of meliorating inflammation and of inhibiting joint deterioration in mammals therewith. The active ingredients of the novel compositions of this invention may be represented by the following structural formula:

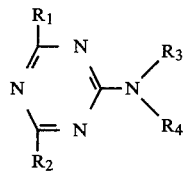

wherein $R_1$ is alkylamino having from 4 to 8 carbon atoms, inclusive, 1-adamantylamino, 2-adamantylamino, exo[2.2.1]norbornylamino or endo[2.2.1]norbornylamino; $R_2$ is 1-adamantylamino, 2-adamantylamino, exo[2.2.1]norbornylamino or endo[2.2.1]norobornylamino; $R_3$ is hydrogen or alkyl having from 1 to 4 carbon atoms, inclusive; $R_4$ is 2-[2-pyridyl]ethyl, alkyl having from 4 to 8 carbon atoms, inclusive, phenyl, monohalo(F, Cl, Br)phenyl, 1-adamantyl, 2-adamantyl, exo[2.2.1]norbornyl, endo[2.2.1]norbornyl or a monovalent moiety of the formula:

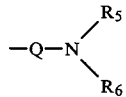

wherein Q is a divalent moiety of the formulae:

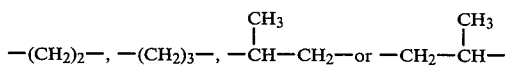

$R_5$ is alkyl having up to 4 carbon atoms, $R_6$ is alkyl having up to 4 carbon atoms, and $R_5$ and $R_6$ taken together with their associated N(itrogen) is piperidino, morpholino, pyrrolidino or thiomorpholino with the proviso that when $R_4$ is alkyl, adamantyl or norbornyl then $R_3$ must be hydrogen; and $R_3$ and $R_4$ taken together with their associated N(itrogen) is pyrrolidino, piperidino, hexamethyleneimino, heptamethyleneimino or a monovalent moiety of the formula:

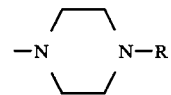

wherein R is hydrogen, alkyl having up to 4 carbon atoms, phenyl, p-methoxyphenyl or carboalkoxy having up to 4 carbon atoms.

DETAILED DESCRIPTION OF THE INVENTION

The active compounds of the present invention are obtainable as crystalline materials having characteristic melting points and absorption spectra. They are appreciably soluble in many organic solvents such as lower alkanols, acetone, ethyl acetate, and the like, but are generally insoluble in water. These compounds are capable of forming acid-addition and quaternary ammonium salts with a variety of organic and inorganic salt-forming reagents when the substituent —$NR_3R_4$ contains a basic nitrogen atom. Thus, acid-addition salts, formed by admixture of the organic free base with an equivalent of an acid, suitably in a neutral solvent, are formed with such acids as sulfuric phosphoric, hydrochloric, hydrobromic, citric, tartaric, acetic, and related acids. In like manner, quaternary ammonium salts may be formed by reaction of the free bases with an equivalent of a variety of organic esters of sulfuric, hydrohalic and aromatic sulfonic acids. The organic reagents employed for quaternary ammonium salt formation are preferably lower alkyl halides. The acid-addition and quaternary ammonium salts of the active compounds of the present invention are, in general, crystalline solids relatively soluble in water, methanol and ethanol but relatively insoluble in non-polar organic solvents such as diethyl ether, benzene, toluene, and the like. For purposes of this invention, the free bases are equivalent to their non-toxic acid-addition and quaternary ammonium salts.

The $N_2$, $N_4$, $N_6$-tris(substituted)melamines of the novel compositions of the present invention may be readily prepared from cyanuric chloride (I) as set forth in the following reaction scheme:

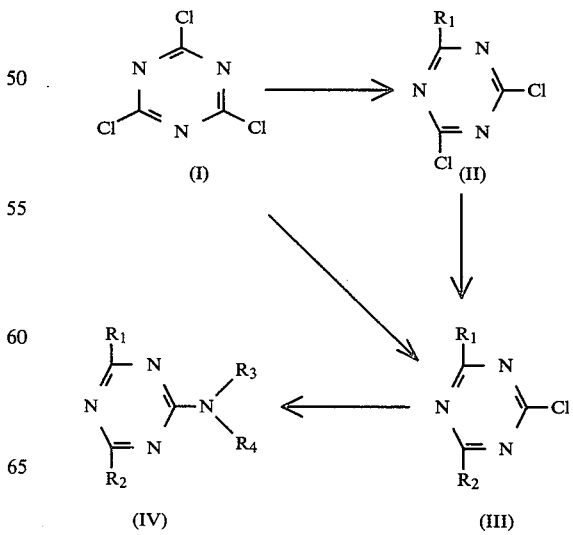

wherein $R_1$, $R_2$, $R_3$ and $R_4$ are as hereinabove defined. In accordance with the above reaction scheme, cyanuric chloride (I) is reacted with one molecular equivalent of an amine of the formula $R_1H$ to provide the corresponding 2-(substituted-amino)-4,6-dichloro-s-triazine (II). Treatment of (II) with one molecular equivalent of an amine of the formula $R_2H$ then provides the corresponding 2-chloro-4,6-bis(substituted-amino)-s-triazine (III). Treatment of the latter intermediate with an amine of the formula:

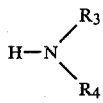

wherein $R_3$ and $R_4$ are as hereinabove defined then provides the active compounds (IV) of the present invention. The above reactions may be carried out in an inert solvent such as soluene or xylene for a period of time of from about 3 hours to 24 hours or more at temperatures ranging from about 25° C. to about 200° C. In addition, α-pyridone may be employed as catalyst in solvents or as a reaction medium. Variation in the reaction time and temperature is dependent upon the structure of the amine reagents; and an acid scavenger such as sodium bicarbonate, soda ash, or a tertiary amine such as diisopropylethylamine should be employed to take up the hydrochloric acid produced in the reaction. In those cases where an excess of amine may be used, then an acid scavenger and/or an inert solvent may be dispensed with. Where $R_1$ and $R_2$ are the same, then treatment of (I) with two molecular equivalents of amine provides the intermediate (III) directly.

The active compounds of the present invention have been found to be highly useful for meliorating inflammation and associated joint deterioration in mammals when administered in amounts ranging from about one milligram to about 250 mg. per kilogram of body weight per day. A preferred dosage regimen for optimum results would be from about 5 mg. to about 100 mg. per kilogram of body weight per day, and such dosage units are employed that a total of from about 0.35 gm. to about 7.0 gm. of the active ingredient for a subject of about 70 kg. of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. A decided practical advantage of this invention is that the active ingredient may be administered in any convenient manner such as by the oral, intravenous, intramuscular, topical, or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatime, normally liquid, polyethylene glycols which are soluble in both water and organic liquids and which have molecular weights of from about 200 to 1500. Although the amount of active compound dissolved in the above vehicle may vary from 0.10% to 10.0% by weight, it is preferred that the amount of active compound employed be from about 3.0% to about 9.0% by weight. Although various mixtures of the aforementioned nonvolatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, phenyl mercuric nitrate, benzalkonium chloride, phenethyl alcohol, P-chlorophenyl-α-glycerol ether, methyl and propyl parabens, and thimerosal. As a practical matter it is also convenient to employ antioxidants. Suitable antioxidants include, for example, sodium bisulfite, sodium metabisulfits, and sodium formaldehyde sulfoxylate. Generally, from about 0.05% to about 0.2% concentrations of antioxidant are employed.

For intramuscular injection, the preferred concentration of active compound is 0.25 to 0.50 mg./ml. of the finished compositions. These active compounds are equally adapted to intravenous administration when diluted with water or diluents employed in intravenous therapy such as isotonic glucose in appropriate quantities. For intravenous use, initial concentrations down to about 0.05 to 0.25 mg./ml. of active compound are satisfactory.

The active compounds of the present invention may be orally administered, for example, with an inert diluent or with an assimilable edible carrier, or they may be enclosed in hard or soft shell gelatin capsules, or they may be compressed into tablers, or they may be incorporated directly with the food of the diet. For oral therapeutic administration, the active compounds may be incorporated with excipients and used in the form of tablers, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of the unit. The amount of active ingredient in such therapeutically useful compositions is such that a suitable dosage will be obtained. Preferred compositions or preparations according to the present invention are prepared so that an oral dosage unit form contains between about 50 and 250 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

Adjuvant-induced experimental polyarthritis is a specific systemic disease of the rat which shares interesting similarities with rheumatoid arthritis. Specifically, the histology of the two diseases bears a remarkable resemblance as shown by C. M. Pearson et al., Am. J. Pathol. 42, 73 (1963). E. M. Glenn, Am. J. Vet. Res. 27 (116), 339 (1966) has classified adjuvant-induced polyarthritis as a crippling and permanent deformity resulting from diffuse connective tissue involvement around certain susceptible joints in the rat. Zahiri et al., Can. Med. Ass. J. 101, 269 (1969) have shown that the fusiform swelling of the distal joints is associated with edema, congestion and synovitis including pannus formation, all of which precede the ultimate destruction of bone and cartilage. Furthermore, Zahiri et al. indicate that the cartilage destruction in the joint is due to an invasive pannus which originates in the marginal synovium and extends across the articular surface to erode it. When non-steroidal, anti-inflammatory agents such as indomethacin inhibit arthritic paw swelling, which is composed of inflammatory cell infiltrates, they have also been shown to prevent joint and bone deterioration. See S. Wong et al., J. Pharm. & Exptl. Ther. 185, 127 (1973) and G. R. Bobalick et al., Agents & Actions 4, 364 (1974). The most pertinent reference showing the relationship between arthritis and joint deterioration is an X-ray analysis of adjuvant arthritis in the rat by Blackham et al., Agents & Actions 7, 145 (1977). In a similar manner, inhibition of the progress of arthritis in paws of rats treated with the compounds of this invention also lessens associated joint deterioration.

The following test shows the activity of the compounds of this invention against chronic inflammation in adjuvant-induced arthritis which is accompanied by joint destruction. Groups of three Royal Hart, Wistar strain rats weighing 200±10 grams each were injected intradermally in the right hind paw with Freund's adjuvant (dried human tubercle bacilli in a mineral oil behicle) at a dose of 2 mg./kg. of body weight. Test compounds were administered orally in a 1.5% starch vehicle at various doses once daily on days 0 through 13 post challenge. Control rats were treated in a similar manner, but given only starch vehicle. On the 14th and 21st day post challenge the diameter of the injected paw (primary lesion) was measured by micrometer caliper. The volume of inflamed paws were estimated from these measurements and the results are expressed as percent inhibition of swelling as compared to controls. At the same time, the other inflamed sites, such as ears, paws and tail (secondary lesions) were observed and each rat was graded as to degree of inflammation and swelling present. The grading is based on a scale of 0 to 24 where 0 represents a complete absence of induced arthritic nodules and 24 represents the maximum degree of inflammation. The mean grade for each treated group is calculated and the effects of each compound are expressed as percent inhibition of the control grade. Table I below records the results of tests conducted with the active compounds of this invention and known anti-inflammatory agents. The active compounds of this invention appear to suppress the progression of the arthritis and associated joint deterioration.

TABLE I

The Effect of Anti-Inflammatory Agents on Adjuvant Arthritis In Rats

| Compound | Oral Dose mg./kg. of Body Wgt. | Dead/Treated at 21 Days | Mean Weight Gain (grams) Day 14 | Mean Weight Gain (grams) Day 21 | % Inhibition of Swelling (primary lesion) Day 14 | % Inhibition of Swelling (primary lesion) Day 21 | % Inhibition of Control Grade (secondary lesion) Day 14 | % Inhibition of Control Grade (secondary lesion) Day 21 |
|---|---|---|---|---|---|---|---|---|
| Normal rats | — | 8/186 | 77 | 112 | — | — | — | — |
| Adjuvant Controls | — | 56/630 | 36 | 31 | 0 | 0 | 0 | 0 |
| $N^2$—(1-adamantyl)-$N^4$,$N^6$—bis(1,1,2,2-tetramethylpropyl)melamine | 50 | 1/12 | 94 | 89 | 47 | 17 | — | — |
| $N^2$—(2-adamantyl)-$N^4$,$N^6$—bis(1,1,2,2-tetramethylpropyl)melamine | 50 | 1/3 | 148 | 181 | 79 | 83 | — | — |
| $N^2$—(exo[2.2.1]norbornyl)-$N^4$,$N^6$—bis(1,1,2,2-tetramethylpropyl)melamine | 50 | 0/3 | 97 | 93 | 49 | 24 | — | — |
| Indomethacin | 2 | 8/57 | 68 | 68 | 51 | 24 | 38 | 25 |
| | 1 | 9/54 | 63 | 65 | 46 | 19 | 34 | 20 |
| | 0.5 | 5/54 | 53 | 51 | 40 | 20 | 25 | 17 |
| | 0.25 | 0/9 | 51 | 57 | 30 | 4 | 22 | 4 |
| Aspirin | 400 | 18/57 | 41 | 55 | 73 | 48 | 58 | 45 |
| | 200 | 10/66 | 40 | 44 | 48 | 27 | 26 | 17 |
| | 100 | 18/63 | 48 | 53 | 36 | 13 | 19 | 8 |
| | 50 | 2/21 | 56 | 44 | 23 | 3 | 12 | 9 |
| Phenylbutazone | 150 | 2/27 | 40 | 50 | 75 | 44 | 54 | 31 |
| | 75 | 2/39 | 51 | 50 | 62 | 28 | 27 | 15 |
| | 37.5 | 5/39 | 53 | 53 | 56 | 14 | 18 | 13 |
| | 18.8 | 2/21 | 50 | 45 | 31 | 7 | 4 | 8 |

The invention will be described in greater detail in conjunction with the following specific examples.

EXAMPLE 1

Preparation of 50 mg. Tablets

| Per Tablet | | Per 10,000 Tablets |
|---|---|---|
| 0.050 gm. | 2-(1-adamantylamino)-4,6-bis(1,1,2,2-tetramethyl-butylamino)-s-triazine | 500 gm. |
| 0.080 gm. | Lactose | 800 gm. |
| 0.010 gm. | Corn Starch (for mix) | 100 gm. |
| 0.008 gm. | Corn Starch (for paste) | 75 gm. |
| 0.148 gm. | | 1475 gm. |
| 0.002 gm. | Magnesium Stearate (1%) | 15 gm. |
| 0.150 gm. | | 1490 gm. |

The 2-(1-adamantylamino)-4,6-bis(1,1,2,2-tetramethylbutylamino)-s-triazine, lactose and corn starch (for mix) are blended together. The corn starch (for paste) is suspended in 600 ml. of water and heated with stirring to form a paste. This paste is then used to granulate the mixed powders. Additional water is used if necessary. The wet granules are passed through a No. 8 hand screen and dried at 120° F. The dry granules are then passed through a No. 16 screen. The mixture is lubricated with 1% magnesium stearate and compressed into tablers in a suitable tableting machine.

EXAMPLE 2

Preparation of Oral Suspension

| Ingredient | Amount |
| --- | --- |
| 2-(2-adamantylamino)-4,6-bis(1,1,3-trimethylbutylamino)-s-triazine | 500 mg. |
| Sorbitol solution (70% N.F.) | 40 ml. |
| Sodium benzoate | 150 mg. |
| Saccharin | 10 mg. |
| Red dye | 10 mg. |
| Cherry flavor | 50 mg. |
| Distilled water gs ad | 100 ml. |

The sorbitol solution is added to 40 ml. of distilled water and the 2-(2-adamantylamino)-4,6-bis(1,1,3-trimethylbutylamino)-s-triazine is suspended therein. The succharin, sodium benzoate, flavor and dye are added and dissolved. The solume is adjusted to 100 ml. with distilled water. Each ml. of syrup contains 5 mg. of 2-(2-adamantylamino)-4,6-bis(1,1,3-trimethylbutylamino)s-triazine.

EXAMPLE 3

Preparation of Parenteral Solution

In a solution of 700 ml. of propylene glycol and 200 ml. of water for injection is suspended 20.0 grams of $N^2$-(exo[2.2.1]norbornyl)-$N^4$,$N^6$-bis(1,1,4-trimethylpentyl)melamine with stirring. After suspension is complete the pH is adjusted to 5.5 with hydrochloric acid and the volume is made up to 1000 ml. with water for injection. The formulation is sterilized, filled into 5.0 ml. ampoules each containing 2.0 ml. (representing 40 mg. of drug) and sealed under nitrogen.

EXAMPLE 4

Preparation of Topical Cream

| Ingredient | Amount |
| --- | --- |
| 2-(endo[2.2.1]norbornylamino)-4,6-bis(1,1,2,2-tetramethylbutylamino)-s-triazine | 1.0% |
| Ethoxylated stearyl alcohol | 10.0% |
| Benzyl alcohol | 0.9% |
| Isopropyl palmitate | 5.0% |
| Glycerin | 5.0% |
| Sorbitol solution (USP) | 5.0% |
| Lactic acid gs to pH 4.0–5.0 | |
| Water gs ad | 100.00% |

The ethoxylated stearyl alcohol and isopropyl palmitate are heated to liquifying temperature. About 95% of the total volume of water is placed in a separate container followed by the flycerin and sorbitol solution. This aqueous mixture is brought to a boil and then cooled to 60°–75° C. The 2-(endo[2.2.1]norbornylamino)-4,6-bis(1,1,2,2-tetramethylbutylamino)-s-triazine adjusted to 4.0–5.0 with lactic acid. The batch is cooled with minimum agitation until the cream sets in its final form.

EXAMPLE 5

Preparation of Injectable Depo Suspension

| Ingredient | % W/V |
| --- | --- |
| $N^2$—(1-adamantyl)-$N^4$, $N^6$—bis(1,1,2,2-tetramethylbutyl)melamine | 0.05–5 |
| Polysorbate 80 USP | 0.2 |
| Polyethylene glycol 4000 USP | 3.0 |
| Sodium chloride USP | 0.8 |
| Benzyl alcohol N.F. | 0.9 |
| HCL to pH 6–8 | qs |
| Water for injection qs ad | 100.0 |

EXAMPLE 6

Preparation of $N^2$-1-adamantyl-$N^4$,$N^6$-bis(1,1,2,2-tetramethylpropyl)-melamine Seven grams (0.02 mole) of 2-chloro-4,6-bis[1,1,2,2-tetramethylpropyl)amino]-s-triazine is ground up in a mortar and 24 g. (0.16 mole) of 1-adamantylamine is intimately mixed, placed in a glass liner in a bomb and then heated in an oil bath maintained at 210°–220° C. for 20 hours. After cooling, the contents of the bomb are rinsed with chloroform and water into a flask and 50 ml. of 10N NaOH is added. The solution is then evaporated in vacuo and the aqueous solution remaining is extracted with chloroform. The combined chloroform extracts are washed with water, dried over magnesium sulfate, filtered through Magnesol ® and the Magnesol ® washed with chloroform. Removal of solvent in vacuo, addition of toluene and re-evaporation in vacuo several times gives 28 g. of solid. Column chromatography os this solid on silica gel and recrystallization of the pure fractions containing the least polar component from acetone give 7.9 g. of colorless crystals m.p. 215.5°–218° C.

EXAMPLE 7

Preparation of $N^2$-2-adamantyl-$N^4$,$N^6$-bis(1,1,2,2-tetramethylpropyl)-melamine Seven grams (0.02 mole) of 2-chloro-4,6-bis[(1,1,2,2-tetramethylpropyl)amino]-s-triazine, 7.7 g. (0.041 mole) of 2-adamantylamine hydrochloride, 11 ml. (0.061 mole) of N,N-diisopropylethylamine and xylene are refluxed under an argon atmosphere for 20 hours. After cooling, the reaction is diluted with ethyl acetate and water. The mixture is then washed with water, the organic phase dried over magnesium sulphate, filtered through diatomaceous earth and evaporated in vacuo to give a pale yellow solid, 11 g. This solid is then dissolved in dichloromethane and filtered through Magnesol ®. Evaporation of the solvent in vacuo and recrystallization from n-heptane gives 3.0 g. of colorless crystals, m.p. 244°–249° C.

EXAMPLE 8

Preparation of exo-$N^2$-2-norbornyl-$N^4$,$N^6$-bis[(1,1,2,2-tetramethylpropyl)amino]-melamine Seven grams (0.02 mole) of 2-chloro-4,6-bis[(1,1,2,2-tetramethylpropyl)amino]-s-triazine and 24 ml. (0.2 mole) of exo-2-norbornylamine is placed in a glass liner in a bomb and then heated in an oil bath maintained at 185°–195° C. for 19–20 hours. After cooling, the contents of the bomb are rinsed with chloroform and water into a flask and 50 ml. of 10N NaOH is added. The solution is then evaporated in vacuo and the aqueous solution remaining is extracted with chloroform. The combined chloroform extracts are washed with water, dried over magnesium sulfate, filtered through Magnesol ® and the Magnesol ® washed with chloroform. Removal of solvent in vacuo and recrystallization from acetone gives 7 g. of colorless crystals, m.p. 159°–163° C.

We claim:

1. The method of inhibiting the progression of arthritis in a mammal which comprises administering to said mammal an effective amount of a compound selected from the group consisting of those of the formula:

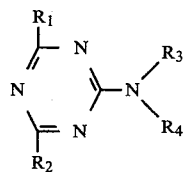

wherein $R_1$ is alkylamino having from 4 to 8 carbon atoms, inclusive, 1-adamantylamino, 2-adamantylamino, exo[2.2.1]norbornylamino or endo[2.2.1]norbornylamino; $R_2$ is 1-adamantylamino, 2-adamantylamino, exo[2.2.1]norbornylamino or endo[2.2.1]norbornylamino; $R_3$ is hydrogen or alkyl having from 1 to 4 carbon atoms, inclusive; $R_4$ is 2-(2-pyridyl)ethyl, alkyl having from 4 to 8 carbon atoms, inclusive, phenyl, monohalo(F, Cl, Br)phenyl, 1-adamantyl, 2-adamantyl, exo[2.2.1]norbornyl,endo[2.2.1]norbornyl or a monovalent moiety of the formula:

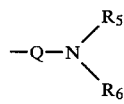

wherein Q is a divalent moiety of the formulae:

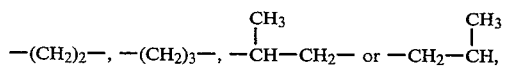

$R_5$ is alkyl having up to 4 carbon atoms, $R_6$ is alkyl having up to 4 carbon atoms, and $R_5$ and $R_6$ taken together with their associated N(itrogen) is piperidino, morpholino, pyrrolidino or thiomorpholino with the proviso that when $R_4$ is alkyl adamantyl or norbornyl then $R_3$ must be hydrogen; and $R_3$ and $R_4$ taken together with their associated N(itrogen) is pyrrolidino, piperidino, hexamethyleneimino, heptamethyleneimino or a monovalent moiety of the formula:

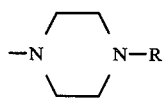

wherein R is hydrogen, alkyl having up to 4 carbon atoms, phenyl, p-methoxyphenyl or carboalkoxy having up to 4 carbon atoms; and the non-toxic acid-addition and quaternary ammonium salts thereof.

2. The method of inhibiting the progressive joint deterioration in a mammal which comprises administering to said mammal an effective amount of a compound selected from the group consisting of those of the formula:

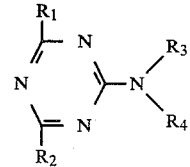

wherein $R_1$ is alkylamino having from 4 to 8 carbon atoms, inclusive, 1-adamantylamino, 2-adamantylamino,exo[2.2.1]norbornylamino or endo[2.2.1]norbornylamino; $R_2$ is 1-adamantylamino, 2-adamantylamino, exo[2.2.1]norbornylamino or endo[2.2.1]norbornylamino; $R_3$ is hydrogen or alkyl having from 1 to 4 carbon atoms, inclusive; $R_4$ is 2-(2-pyridyl)ethyl, alkyl having from 4 to 8 carbon atoms, inclusive, phenyl, monohalo(F, Cl, Br)phenyl, 1-adamantyl, 2-adamantyl, exo[2.2.1]norbornyl, endo[2.2.1]norbornyl or a monovalent moiety of the formula:

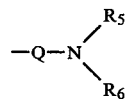

wherein Q is a divalent moiety of the formulae:

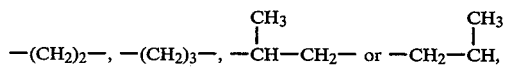

$R_5$ is alkyl having up to 4 carbon atoms, $R_6$ is alkyl having up to 4 carbon atoms, and $R_5$ and $R_6$ taken together with their associated N(itrogen) is piperidino, morpholino, pyrrolidino or thiomorpholino with the proviso that when $R_4$ is alkyl adamantyl or norbornyl then $R_3$ must be hydrogen; and $R_3$ and $R_4$ taken together with their associated N(itrogen) is pyrrolidino, piperidino, hexamethyleneimino, heptamethyleneimino or a monovalent moiety of the formula:

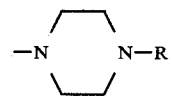

wherein R is hydrogen, alkyl having up to 4 carbon atoms, phenyl, p-methoxyphenyl or carboalkoxy having up to 4 carbon atoms; and the non-toxic acid-addition and quaternary ammonium salts thereof.

3. The method of meliorating inflammation in a mammal which comprises administering to said mammal an effective amount of a compound selected from the group consisting of those of the formula:

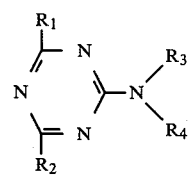

wherein $R_1$ is alkylamino having from 4 to 8 carbon atoms, inclusive, 1-adamantylamino, 2-adamantylamino, exo[2.2.1]norbornylamino or endo[2.2.1]norbornylamino; $R_2$ is 1-adamantylamino, 2-adamantylamino, exo[2.2.1]norbornylamino or endo[2.2.1]norbornylamino; $R_3$ is hydrogen or alkyl having from 1 to 4 carbon atoms, inclusive; $R_4$ is 2-(2-pyridyl)ethyl, alkyl having from 4 to 8 carbon atoms, inclusive, phenyl, monohalo(F, Cl, Br)phenyl, 1-adamantyl, 2-adamantyl, exo[2.2.1]norbornyl, endo[2.2.1]norbornyl or a monovalent moiety of the formula:

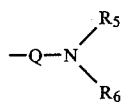

wherein Q is a divalent moiety of the formulae:

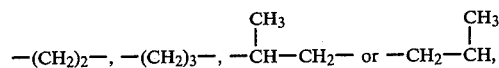

$R_5$ is alkyl having up to 4 carbon atoms, $R_6$ is alkyl having up to 4 carbon atoms, and $R_5$ and $R_6$ taken together with their associated N(itrogen) is piperidino, morpholino, pyrrolidino or thiomorpholino with the proviso that when $R_4$ is alkyl adamantyl or norbornyl then $R_3$ must be hydrogen; and $R_3$ and $R_4$ taken together with their associated N(itrogen) is pyrrolidino, piperidino, hexamethyleneimino, heptamethyleneimino or a monovalent moiety of the formula:

wherein R is hydrogen, alkyl having up to 4 carbon atoms, phenyl, p-methoxyphenyl or carboalkoxy having up to 4 carbon atoms; and the non-toxic acid-addition and quaternary ammonium salts thereof.

* * * * *